United States Patent
Toida (10) Patent No.: US 10,809,200 B2
(45) Date of Patent: Oct. 20, 2020

(54) TEST OBJECT VISUALIZING DEVICE

(71) Applicant: Saitama Medical University, Saitama (JP)

(72) Inventor: Masahiro Toida, Saitama (JP)

(73) Assignee: SAITAMA MEDICAL UNIVERSITY, Iruma-Gun, Saitama (JP)

( * ) Notice: Subject to any disclaimer, the term of this patent is extended or adjusted under 35 U.S.C. 154(b) by 32 days.

(21) Appl. No.: 16/309,732

(22) PCT Filed: Jun. 16, 2017

(86) PCT No.: PCT/JP2017/022295
§ 371 (c)(1),
(2) Date: Dec. 13, 2018

(87) PCT Pub. No.: WO2017/217534
PCT Pub. Date: Dec. 21, 2017

(65) Prior Publication Data
US 2019/0137402 A1 May 9, 2019

(30) Foreign Application Priority Data

Jun. 17, 2016 (JP) .................. 2016-121108

(51) Int. Cl.
*G01N 21/65* (2006.01)
*A61B 5/00* (2006.01)
*A61B 3/10* (2006.01)

(52) U.S. Cl.
CPC ........... *G01N 21/65* (2013.01); *A61B 5/0066* (2013.01); *A61B 3/10* (2013.01); *G01N 2021/653* (2013.01)

(58) Field of Classification Search
CPC .............. G01B 9/02091; A61B 5/0066; G01N 2021/653
See application file for complete search history.

(56) References Cited

U.S. PATENT DOCUMENTS 5,870,188 A 2/1999 Ozaki et al.
2008/0117416 A1* 5/2008 Hunter ................. A61B 5/0066
356/301

(Continued)

FOREIGN PATENT DOCUMENTS

EP 2 821 016 A1 1/2015
JP H09-145619 A 6/1997
(Continued)

OTHER PUBLICATIONS

Kebin Shi,"Coherent Anti-Stokes Raman Holography for Chemically Selective Single-Shot Nonscanning 3D Imaging", 2010, American Physical Society (Year: 2010).*

(Continued)

*Primary Examiner* — Maurice C Smith
(74) *Attorney, Agent, or Firm* — Buchanan, Ingersoll & Rooney PC (57) ABSTRACT

Provided is a test object visualizing device, including: light irradiating unit configured to make wavelength of at least any one of pump light and Stokes light generated on the same optical path variable per test position of test object, and irradiate test object with pump light and Stokes light; molecule distribution image generating unit configured to detect anti-Stokes light emitted from test object according to wavelength difference between pump light and Stokes light, and generate a molecule distribution image based on anti-Stokes light; tomographic image generating unit configured to detect at least any one of reflected light from test object when irradiated with pump light and reflected light from test object when irradiated with Stokes light, and generate a tomographic image of test object based on the reflected light detected; and image display unit configured to display at least any one of molecule distribution image and tomographic image generated.

7 Claims, 4 Drawing Sheets

(56) References Cited

U.S. PATENT DOCUMENTS

| | | | |
|---|---|---|---|
| 2011/0116158 A1 | 5/2011 | Dunn et al. | |
| 2011/0128538 A1 | 6/2011 | Cerullo et al. | |
| 2013/0038871 A1* | 2/2013 | Rigneault | G01J 3/4412 |
| | | | 356/301 |
| 2014/0253919 A1 | 9/2014 | Yui | |
| 2015/0005641 A1 | 1/2015 | Toida | |

FOREIGN PATENT DOCUMENTS

| | | |
|---|---|---|
| JP | 2011-170212 A | 9/2011 |
| JP | 2015-141282 A | 8/2015 |

OTHER PUBLICATIONS

Claudio Vinegoni, "Nonlinear optical contrast enhancement for optical coherence tonnography",2004,Optics Express (Year: 2004).*

Tschackad Kannali,"Hybrid single-source online Fourier transform coherent anti-Stokes Raman scattering/optical coherence tonnography",Optical Society of America, 2014 (Year: 2014).*

The Extended European Search Report dated Dec. 18, 2019, by the European Patent Office in corresponding European Patent Application No. 17813428.4. (13 pages).

Evans et al., "Coherent Anti-Stokes Raman Scattering Microscopy: Chemical Imaging for Biology and Medicine," Annual Review of Analytical Chemistry, Jul. 1, 2008, vol. 1, No. 1, pp. 883-909.

Hoffmann et al., "Combined OCT and CARS using a single ultrashort pulse Ti:Sapphire Laser," Multimodal Biomedical Imaging VI, SPIE, Feb. 10, 2011, vol. 7892, No. 1, pp. 1-8.

Jones et al., "High-spectral-resolution coherent anti-Stokes Raman scattering with interferometrically detected broadband chirped pulses," Optics Letters, May 15, 2006, vol. 31, No. 10, pp. 1543-1545.

Zhou et al., "Lasers Based on Optical Parametric Devices: Wavelength Tunability Empowers Laser-Based Techniques in the UV, Visible, and Near-IR," Applied Spectroscopy, May 5, 1998, vol. 52, No. 5, pp. 176A-189A.

International Search Report (PCT/ISA/210) dated Sep. 19, 2017, by the Japan Patent Office as the International Searching Authority for International Application No. PCT/JP2017/022295.

Written Opinion (PCT/ISA/237) dated Sep. 19, 2017, by the Japan Patent Office as the International Searching Authority for International Application No. PCT/JP2017/022295.

Notification of Transmittal of the International Preliminary Report on Patentability (Form PCT/IPEA/416) and International Preliminary Report on Patentability (Chapter II) (Form PCT/IPEA/409) dated Mar. 16, 2018, by the Japanese Patent Office for International Application No. PCT/JP2017/022295.

* cited by examiner

TEST OBJECT VISUALIZING DEVICE

TECHNICAL FIELD

The present invention relates to a test object visualizing device configured to visualize a molecule distribution image and a cross-section of a test object.

BACKGROUND ART

In recent years, the genetic diagnosis has made a remarkable progress and brought about an era in which it is possible to judge what disease risks individuals genetically have or not. However, because it is impossible to also judge the time when a disease will occur, it is important to discover the occurrence of a disease in a less invasive manner in an early stage of the disease and realize a less invasive treatment.

For discovery of a disease in its early stage, it is important to identify a functional change of a test object at a previous stage before the test object undergoes a morphological change. In order to identify a functional change, molecule distribution imaging techniques capable of visualizing the distribution of the molecules of, for example, a specific protein in a cell or in a tissue in vivo are effective.

The molecule distribution imaging techniques using light are roughly classified into probe methods using, for example, a fluorescent labeling drug and non-probe methods using a characteristic of a substance intrinsic in a living body. Of the non-probe methods, the molecule distribution imaging techniques utilizing CARS (Coherent Anti-Stokes Raman Scattering) are being studied.

In elucidation of the occurring mechanism and the developing mechanism of each disease, detailed spatial position information of molecules in the test object is indispensable in order to identify a morphological change of the test object. Hence, the molecule distribution imaging techniques corresponding to the spatial position information are demanded.

OCT (Optical Coherence Tomography) has been developing as a noninvasive living body morphological imaging technique capable of obtaining the spatial position information. Hence, studies are being made into combined use of the molecule distribution imaging technique utilizing CARS and the morphological imaging technique utilizing OCT. The present inventor has also proposed an idea for it (for example, see PTL 1).

CITATION LIST

Patent Literature

PTL 1: Japanese Patent Application Laid-Open (JP-A) No. 2015-141282

SUMMARY OF INVENTION

Technical Problem

The present invention aims for solving the various problems in the related art and achieving an object described below. That is, the present invention has an object to provide a test object visualizing device capable of simultaneously capturing a molecule distribution image and a tomographic image of a test object.

Solution to Problem

Means for solving the above problems are as follows.
<1> A test object visualizing device, including:
a light irradiating unit configured to make a wavelength of at least any one of pump light and Stokes light variable per test position of a test object, the pump light and the Stokes light being generated on a same optical path, the light irradiating unit being configured to irradiate the test object with the pump light and the Stokes light;
a molecule distribution image generating unit configured to detect anti-Stokes light emitted from the test object according to a wavelength difference between the pump light and the Stokes light, and generate a molecule distribution image based on the anti-Stokes light;
a tomographic image generating unit configured to detect at least any one of reflected light from the test object when the test object is irradiated with the pump light and reflected light from the test object when the test object is irradiated with the Stokes light, and generate a tomographic image of the test object based on the reflected light detected; and
an image display unit configured to display at least any one of the molecule distribution image and the tomographic image that are generated.

In the test object visualizing device according to <1>, the light irradiating unit is configured to make the wavelength of at least any one of the pump light and the Stokes light, which are generated on the same optical path, variable per test position of a test object, and irradiate the test object with the pump light and the Stokes light. The molecule distribution image generating unit is configured to detect the anti-Stokes light emitted from the test object according to the wavelength difference between the pump light and the Stokes light, and generate a molecule distribution image based on the anti-Stokes light. The tomographic image generating unit is configured to detect at least any one of reflected light from the test object when the test object is irradiated with the pump light and reflected light from the test object when the test object is irradiated with the Stokes light, and generate a tomographic image of the test object based on the reflected light detected. The image display unit is configured to display at least any one of the molecule distribution image and the tomographic image that are generated.

By the light irradiating unit generating the pump light and the Stokes light on the same optical path, a mirror or a space for adjusting the optical path length from the light exit to the test object becomes unnecessary, as compared with a case where the pump light and the Stokes light are generated on different optical paths, making it possible to downsize the test object visualizing device.

By the test object visualizing device irradiating the test object with the pump light and the Stokes light by making the wavelength of at least any one of the pump light and the Stokes light, which are generated on the same optical path, variable per test position of the test object, a tomographic image of the test object is generated based on at least any one of reflected light from the test object when the test object is irradiated with the pump light and reflected light from the test object when the test object is irradiated with the Stokes light, and a molecule distribution image is generated based on the anti-Stokes light, making it possible to simultaneously capture the molecule distribution image and the tomographic image. By scanning the pump light and the Stokes light in X and Y directions, it is possible to capture the molecule distribution image and the tomographic image that are three-dimensional.

<2> The test object visualizing device according to <1>,
wherein the light irradiating unit is configured to irradiate the test object with the pump light and the Stokes light in a manner that the wavelength difference between the pump light and the Stokes light becomes 0 in ranges in which the wavelength of the pump light and the wavelength of the Stokes light are made variable, and wherein the tomographic image generating unit is configured to generate the tomographic image based on data obtained by merging, at a wavelength at which the wavelength difference becomes 0, data based on the reflected light from the test object when the test object is irradiated with the pump light with data based on the reflected light from the test object when the test object is irradiated with the Stokes light.

In the test object visualizing device according to <2>, the light irradiating unit is configured to irradiate the test object with the pump light and the Stokes light in a manner that the wavelength difference between the pump light and the Stokes light becomes 0 in the ranges in which the wavelength of the pump light and the wavelength of the Stokes light are made variable. Hence, by the tomographic image generating unit generating the tomographic image based on data obtained by merging, at the wavelength at which the wavelength difference becomes 0, data based on the reflected light from the test object when the test object is irradiated with the pump light with data based on the reflected light from the test object when the test object is irradiated with the Stokes light, it is possible to increase data of the tomographic image in the depth direction and increase the resolution of the tomographic image.

<3> The test object visualizing device according to <1> or <2>, wherein the molecule distribution image generating unit is configured to execute an inverse Fourier transform operation on a spectral interference signal obtained by spectrally diffracting interference light, the interference light being the anti-Stokes light.

In the test object visualizing device according to <3>, the molecule distribution image generating unit is configured to execute an inverse Fourier transform operation on a spectral interference signal obtained by spectrally diffracting interference light, the interference light being the anti-Stokes light. This makes it possible to generate the molecule distribution image according to Wiener-Khintchine's theorem.

<4> The test object visualizing device according to any one of <1> to <3>, wherein the tomographic image generating unit is configured to execute an inverse Fourier transform operation on a spectral interference signal obtained by spectrally diffracting interference light, the interference light being at least any one of the reflected light from the test object when the test object is irradiated with the pump light and the reflected light from the test object when the test object is irradiated with the Stokes light.

In the test object visualizing device according to <4>, the tomographic image generating unit is configured to execute an inverse Fourier transform operation on a spectral interference signal obtained by spectrally diffracting interference light, the interference light being at least any one of the reflected light from the test object when the test object is irradiated with the pump light and the reflected light from the test object when the test object is irradiated with the Stokes light. This makes it possible to generate the tomographic image according to Wiener-Khintchine's theorem.

<5> The test object visualizing device according to any one of <1> to <4>, wherein the light irradiating unit includes:
a light trapping device including an optical parametric crystal configured to change a wavelength of light according to an angle of incidence of the light, the light trapping device being configured to trap the light; and an optical resonator sharing the optical parametric crystal with the light trapping device and configured to amplify light of which wavelength is changed by the optical parametric crystal.

In the light irradiating unit of the test object visualizing device according to <5>, the light trapping device includes an optical parametric crystal configured to change the wavelength of light according to the angle of incidence of the light, the light trapping device being configured to trap the light. The optical resonator shares the optical parametric crystal with the light trapping device and is configured to amplify light of which wavelength is changed by the optical parametric crystal. This makes it possible for the light to be changed into two wavelengths through angle change of the optical parametric crystal with respect to the direction of the optical axis of the light, and to be amplified by the optical resonator and output as the pump light and the Stokes light. By changing the angle of the optical parametric crystal, it is possible to make the wavelength of the pump light and the wavelength of the Stokes light variable respectively.

<6> The test object visualizing device according to any one of <1> to <5>, wherein the light irradiating unit is configured to make the wavelength of the pump light and the wavelength of the Stokes light variable in a manner that a vibration band of a molecule contained in the test object coincides with the wavelength difference.

In the test object visualizing device according to <6>, the light irradiating unit is configured to make the wavelength of the pump light and the wavelength of the Stokes light variable in a manner that the vibration band of a molecule contained in the test object coincides with the wavelength difference. This makes it possible for the anti-Stokes light to be emitted from the molecule contained in the test object. Therefore, based on the detected anti-Stokes light, the molecule distribution image can be generated. The test object may contain a plurality of molecules.

<7> The test object visualizing device according to <6>, wherein the molecule contained in the test object is at least any one of glucose, retinol, and lutein.

In the test object visualizing device according to <7>, the molecule contained in the test object is at least any one of glucose, retinol, and lutein. This makes it possible to know the distribution of a molecule related with occurrence of age-related macular degeneration in the fundus retina and diagnose an age-related macular degeneration disease in its early stage.

Advantageous Effects of Invention

The present invention can solve the problems in the related art and provide a test object visualizing device capable of simultaneously capturing a molecule distribution image and a tomographic image of a test object.

DESCRIPTION OF EMBODIMENTS (Test Object Visualizing Device)

The test object visualizing device includes a light irradiating unit, a molecule distribution image generating unit, a tomographic image generating unit, and an image display unit, and further includes other units as needed.

<Light Irradiating Unit>

The light irradiating unit is configured to make the wavelength of at least any one of pump light and Stokes light, which are generated on the same optical path, variable per test position of a test object and irradiate the test object with the pump light and the Stokes light.

The test object is not particularly limited and may be appropriately selected depending on the intended purpose. Examples of the test object include the fundus.

The test position means a position of the test object at which it is desired to capture the molecule distribution image and the tomographic image. The test position is simultaneously irradiated with the pump light and the Stokes light. With simultaneous irradiation with the pump light and the Stokes light, anti-Stokes light is emitted according to a wavelength difference between the pump light and the Stokes light. Based on the anti-Stokes light that is detected, the molecule distribution image can be generated.

The wavelength difference means a difference between the wavelength of the pump light and the wavelength of the Stokes light.

When the test position is set at a plurality of positions in the X direction of the test object, the molecule distribution image and the tomographic image that are two-dimensional are obtained. When the test position are set at a plurality of positions in the X and Y directions of the test object, the molecule distribution image and the tomographic image that are three-dimensional can be obtained.

The same optical path means that rays of light pass the same path and pass through the same optical system.

Examples of a method for generating the pump light and the Stokes light on the same optical path include a method based on optical parametric oscillation.

Examples of the method based on optical parametric oscillation include a method of irradiating a nonlinear medium such as an optical parametric crystal with laser light having a predetermined wavelength to generate rays of laser light having different wavelengths.

The pump light is light with which the test object is irradiated in a manner that the energy level of a molecule contained in the test object increases, in order for anti-Stokes light to be emitted from the molecule contained in the test object. The pump light may be referred to as "signal light" in optical parametric oscillation.

The Stokes light is light with which the test object is irradiated in a manner that the energy level of the molecule, which has increased by irradiation with the pump light in order for the anti-Stokes light to be emitted from the molecule contained in the test object, is induced to a predetermined energy level. The Stokes light may be referred to as "idler light" in optical parametric oscillation.

The principle by which the anti-Stokes light is emitted from the molecule contained in the test object by simultaneous irradiation of the test position of the test object with the pump light and the Stokes light will be described below.

The wavelength of at least any one of the pump light and the Stokes light is not particularly limited, may be appropriately selected depending on the intended purpose, and is preferably 980 nm or longer but 1,150 nm or shorter. The wavelength in the preferable range is advantageous, because it is easier to obtain the molecule distribution image and the tomographic image of a deep portion below the fundus retina.

It is preferable that the light irradiating unit irradiate the test object with the pump light and the Stokes light in a manner that the wavelength difference between the pump light and the Stokes light becomes 0 in the ranges in which the wavelength of the pump light and the wavelength of the Stokes light are made variable.

It is preferable that the light irradiating unit make the wavelength of the pump light and the wavelength of the Stokes light variable in a manner that the vibration band of a molecule contained in the test object coincides with the wavelength difference. This makes it possible to cause the anti-Stokes light to be emitted from the molecule contained in the test object, detect the anti-Stokes light, and generate the molecule distribution image.

The test object may contain a plurality of molecules.

The molecule contained in the test object is not particularly limited. For example, a molecule related with a disease may be appropriately selected depending on the intended purpose. The molecule is preferably at least any one of glucose, retinol, and lutein because it is publicly known that glucose, retinol, and lutein are related with an age-related macular degeneration disease.

It is preferable that the light irradiating unit include a light trapping device including an optical parametric crystal configured to change the wavelength of light according to the angle of incidence of the light, the light trapping device being configured to trap the light; and an optical resonator sharing the optical parametric crystal with the light trapping device and configured to amplify light of which wavelength is changed by the optical parametric crystal.

Hence, the light changed into two wavelengths on the same optical path through angle change of the optical parametric crystal with respect to the direction of the optical axis of the light is amplified by the optical resonator and output as the pump light and the Stokes light.

By changing the angle of the optical parametric crystal, it is possible to make the wavelength of the pump light and the wavelength of the Stokes light variable respectively. Further, it is possible to secure efficiency boosting and temporal stability of the optical parametric oscillation and stability of the output positions of the pump light and the Stokes light against wavelength variations, and adapt to the light of any of a nanosecond pulse, a picosecond pulse, and femtosecond pulse.

Efficiency boosting of the optical parametric oscillation is realized by trapping the light by the light trapping device, passing the light through the optical parametric crystal a plurality of times, and securing a length for the action of energy conversion from the light into the pump light and the Stokes light.

Temporal stability of the optical parametric oscillation is realized by making the resonator length of the optical parametric oscillation short. Moreover, optical parametric oscillation adaptable to the light of any of a nanosecond pulse, a picosecond pulse, and a femtosecond pulse is realized by making the optical path length in the light trapping device and the optical path length in the optical resonator equal to each other.

Furthermore, the pump light and the Stokes light in the optical resonator are made to go and return the optical parametric crystal. Therefore, even if changing the angle of the optical parametric crystal with respect to the direction of the optical axis of the light results in fluctuating the position of the optical axis of the light on the going path, the optical axis returns to the original position on the returning path. This makes it possible to keep the output positions of the pump light and the Stokes light unchangeable.

The optical parametric crystal is not particularly limited and may be appropriately selected depending on the intended purpose. Examples of the optical parametric crystal include potassium titanium phosphate (KTP).

<Molecule Distribution Image Generating Unit>

The molecule distribution image generating unit is configured to detect the anti-Stokes light emitted from a molecule contained in the test object according to the wavelength difference between the pump light and the Stokes light, and generate a molecule distribution image based on the anti-Stokes light.

It is preferable that the molecule distribution image generating unit execute an inverse Fourier transform operation on a spectral interference signal obtained by spectrally diffracting interference light, the interference light being the anti-Stokes light.

It is preferable to cause the anti-Stokes light to be emitted from a molecule contained in the test object by, for example, CARS (Coherent Anti-Stokes Raman Scattering).

Next, the CARS will be described with reference to FIG. 1A, FIG. 1B, FIG. 2A, and FIG. 2B.

Figure 1A:
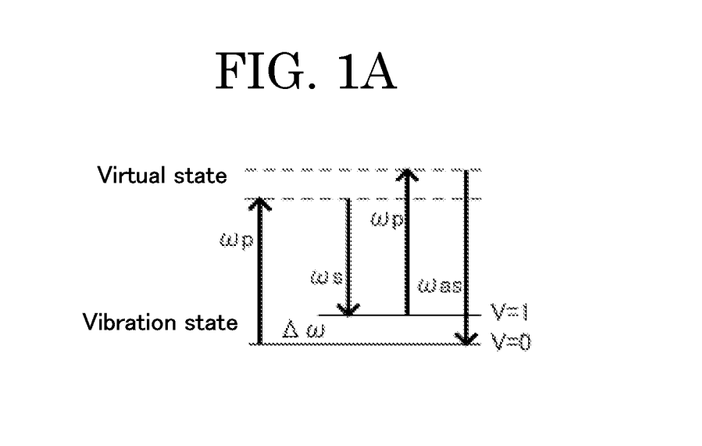
FIG. 1A is a diagram illustrating an energy level process until anti-Stokes light is emitted in CARS.

FIG. 1A is a diagram illustrating an energy level process until anti-Stokes light is emitted in the CARS.

As illustrated in FIG. 1A, the test object is spatiotemporally simultaneously irradiated with pulse oscillated pump light (with an angular frequency $\omega_p$) and pulse oscillated Stokes light (with an angular frequency $\omega_s$). Here, when an angular frequency difference ($\Delta\omega = \omega_p - \omega_s$) between the pump light and the Stokes light coincides with the vibration band of a molecule in the test object, the energy level of the molecule increases from the ground state V=0 to an upper level by the pump light and is induced to an excited level V=1 by the Stokes light. Subsequently, when the test object is irradiated with the pump light, the energy level increases to an even upper level and then decreases to the ground state V=0. During the decreasing process, anti-Stokes light is emitted.

The pulse width of the pump light and the pulse width of the Stokes light are not particularly limited, may be appropriately selected depending on the intended purpose, and are preferably on the picosecond order. This ensures noninvasiveness for the test object, and makes it easier to secure a ratio of the resonance signal to the non-resonance signal (hereinafter may also be referred to as "resonance signal/non-resonance signal ratio").

Figure 1B:
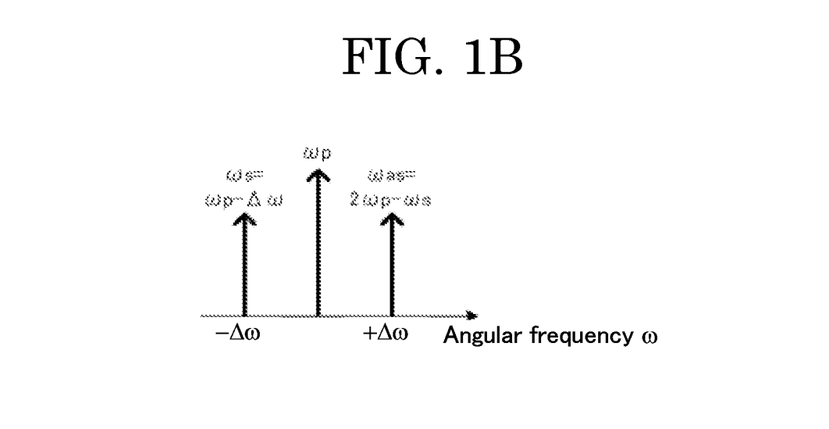
FIG. 1B is a diagram illustrating a relationship among angular frequencies of pump light, Stokes light, and anti-Stokes light.

FIG. 1B is a diagram illustrating a relationship among the angular frequencies of the pump light, the Stokes light, and the anti-Stokes light.

As illustrated in FIG. 1B, the angular frequency $\omega_s$ of the Stokes light and the angular frequency of $\omega_{as}$ of the anti-Stokes light are present at a distance of $\pm\Delta\omega$ from the angular frequency $\omega_p$ of the pump light due to a relation with the energy level. That is, the angular frequency of the Stokes light can be expressed by the following formula: $\omega_s = \omega_p - \Delta\omega$. The angular frequency of the anti-Stokes light can be expressed by the following formula: $\omega_{as} = 2\omega_p - \omega_s = \omega_p + \Delta\omega$.

Figure 2A:
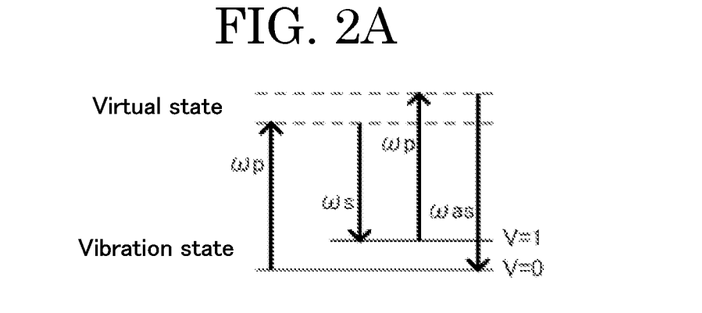
FIG. 2A is a diagram illustrating a resonance process according to which resonant anti-Stokes light occurs when past an excited level V=1 of molecular vibration.
Figure 2B:
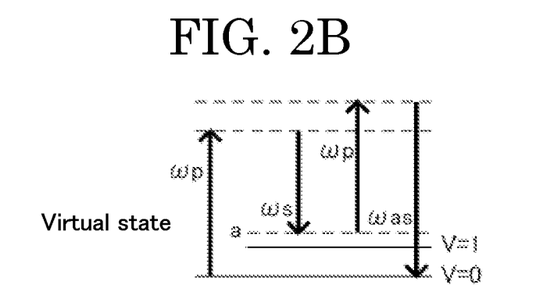
FIG. 2B is a diagram illustrating a non-resonance process according to which non-resonant anti-Stokes light occurs when not past an excited level V=1 of molecular vibration.

FIG. 2A is a diagram illustrating a resonance process according to which resonant anti-Stokes light occurs when past the excited level V=1 of molecular vibration. FIG. 2B is a diagram illustrating a non-resonance process according to which non-resonant anti-Stokes light occurs when not past the excited level V=1 of molecular vibration.

As illustrated in FIG. 2A and FIG. 2B, the anti-Stokes light includes two kinds, namely the resonant anti-Stokes light (hereinafter, may also be referred to as "resonance signal" or simply "anti-Stokes light") and the non-resonant anti-Stokes light (hereinafter, may also be referred to as "non-resonance signal").

The resonant anti-Stokes light that occurs through the resonance process is emitted from the molecule contained in the test object, and used for generation of the molecule distribution image.

The non-resonant anti-Stokes light that occurs through the non-resonance process is a response that is not almost dependent on the wavelength difference and is related with electron excitation of water.

<Tomographic Image Generating Unit>

The tomographic image generating unit is configured to detect at least any one of reflected light from the test object when the test object is irradiated with the pump light and reflected light from the test object when the test object is irradiated with the Stokes light, and generate a tomographic image of the test object based on the detected reflected light.

The tomographic image can be captured according to, for example, OCT (Optical Coherence Tomography). SS-OCT (Swept Source Optical Coherence Tomography) is preferable.

It is preferable that the tomographic image generating unit execute an inverse Fourier transform operation on a spectral interference signal obtained by spectrally diffracting interference light, the interference light being at least any one of the reflected light from the test object when the test object is irradiated with the pump light and the reflected light from the test object when the test object is irradiated with the Stokes light.

<Image Display Unit>

The image display unit is configured to display at least any one of the molecule distribution image and the tomographic image that are generated.

The image display unit is not particularly limited and may be appropriately selected depending on the intended purpose. Examples of the image display unit include a liquid crystal monitor.

<Other Units>

The other units are not particularly limited and may be appropriately selected depending on the intended purpose. It is preferable to provide a signal processing unit.

The signal processing unit is not particularly limited and may be appropriately selected depending on the intended purpose. It is preferable that the signal processing unit merge, at a wavelength at which the wavelength difference becomes 0, data based on the reflected light from the test object when the test object is irradiated with the pump light with data based on the reflected light from the test object when the test object is irradiated with the Stokes light.

Figure 3:
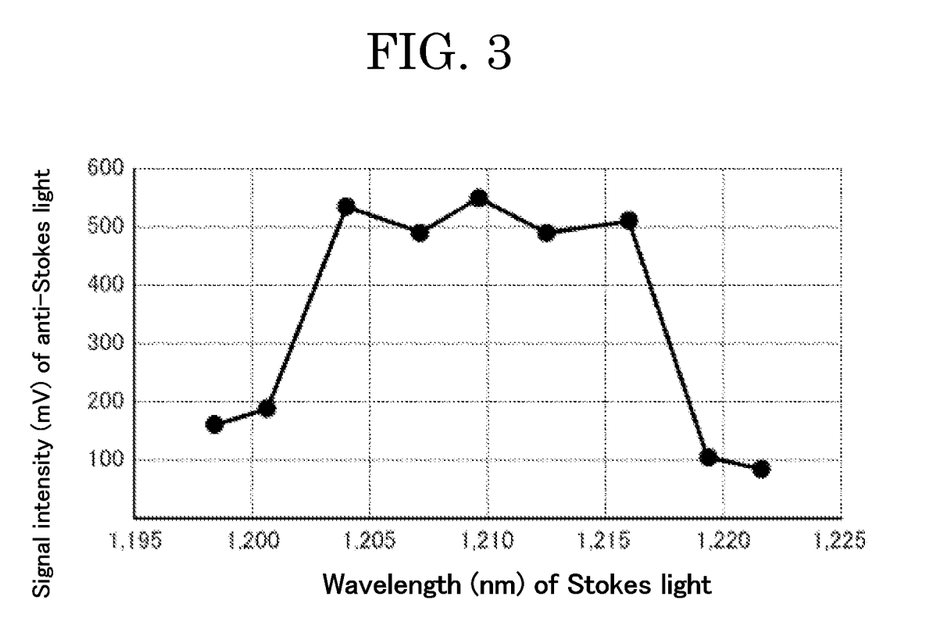
FIG. 3 is a graph plotting dependency of a signal intensity of anti-Stokes light on a wavelength of Stokes light when a glucose solution is irradiated with pump light and Stokes light simultaneously.

FIG. 3 is a graph plotting dependency of the signal intensity of the anti-Stokes light on the wavelength of the Stokes light when a glucose solution is simultaneously irradiated with the pump light and the Stokes light. The vertical axis represents the signal intensity (mV) of the anti-Stokes light and the horizontal axis represents the wavelength (nm) of the Stokes light. FIG. 3 plots the signal intensity of the anti-Stokes light from the glucose solution when the wavelength of the pump light is fixed at 1,064 nm and the wavelength of the Stokes light is varied.

As plotted in FIG. 3, it can be confirmed that the signal intensity of the anti-Stokes light does not fall in Stokes light wavelength range of ±6 nm from 1,209 nm. On this basis, by detecting the anti-Stokes light as the spectral interference signal by a width of about 10 nm while sweeping the wavelength of the Stokes light, it is possible to secure a resolution in the direction of the optical axis of the anti-Stokes light. Moreover, by detecting the reflected light of the Stokes light as the spectral interference signal while sweeping the wavelength of the Stokes light, it is possible to generate the tomographic image because detecting the reflected light of the Stokes light as the spectral interference signal while sweeping the wavelength of the Stokes light is the same as obtaining a spectral interference signal in the depth direction in SS-OCT (Swept Source Optical Coherence Tomography) (hereinafter, the spectral interference signal in the depth direction may also be referred to as "A-line signal").

EXAMPLES

The present invention will be described below by way of Examples. The present invention should not be construed as being limited to these Examples.

Figure 4:
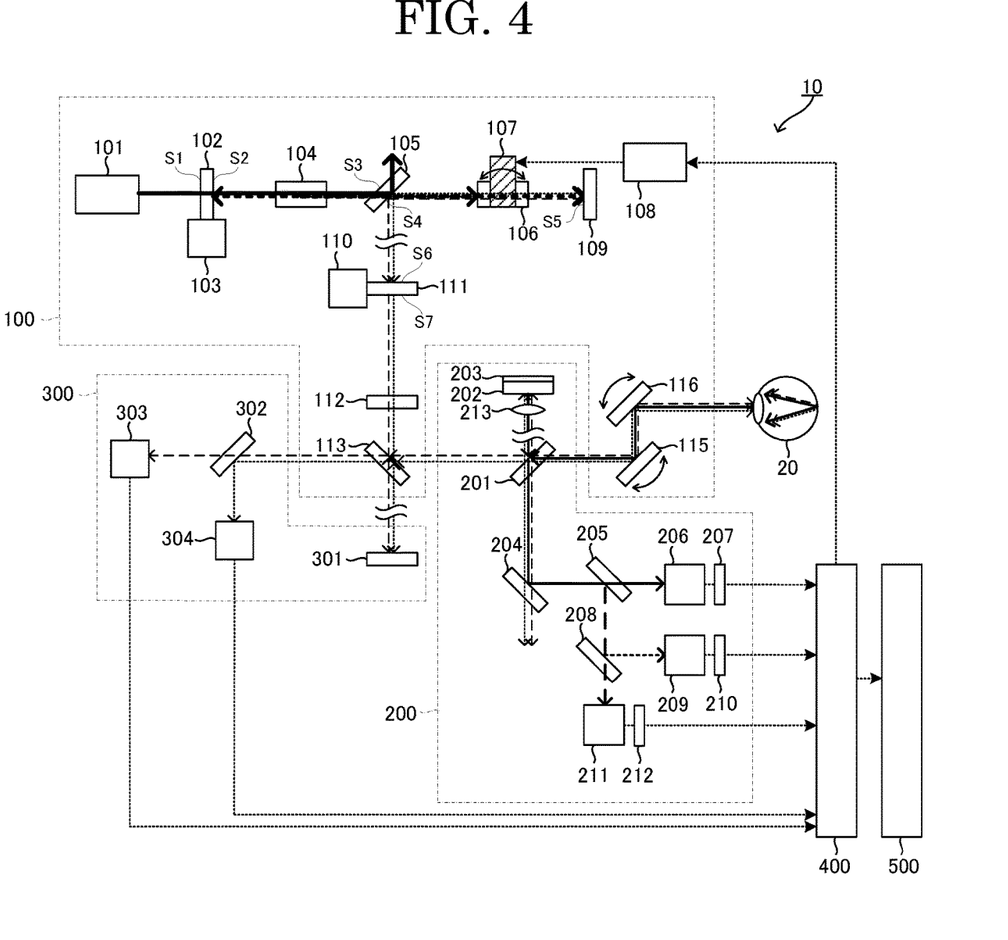
FIG. 4 is a diagram illustrating a test object visualizing device according to an Example.

FIG. 4 is a diagram illustrating a test object visualizing device according to an Example.

As illustrated in FIG. 4, a test object visualizing device 10 includes a light irradiating unit 100, a molecule distribution image generating unit 200, a tomographic image generating unit 300, a signal processing unit 400, and an image display unit 500.

A fundamental wave laser 101 of the light irradiating unit 100 is configured to emit a laser beam having a wavelength of 1,064 nm to a dichroic mirror 102. The laser beam is a mode-locked laser beam with which a picosecond or femtosecond mode is synchronized.

The dichroic mirror 102 has a non-reflection property to light having a wavelength of 1,064 nm on its S1 surface. The dichroic mirror 102 has a non-reflection property to light having a wavelength of 1,064 nm and a total reflection property to light having a wavelength of 532 nm on its S2 surface.

A dichroic mirror 105 has a non-reflection property to light having a wavelength of 532 nm on its S3 surface. The dichroic mirror 105 has a total reflection property to light having a wavelength of from 900 nm through 1,200 nm and a non-reflection property to light having a wavelength of 532 nm on its S4 surface.

A total reflection mirror 109 has a total reflection property to light having a wavelength of from 900 nm through 1,200 nm on its S5 surface.

An output mirror 111 has a 70% PR (partial reflection) property to light having a wavelength of from 900 nm through 1,200 nm and a total reflection property to light having a wavelength of 532 nm on its S6 surface. The output mirror 111 has a non-reflection property to light having a wavelength of from 900 nm through 1,200 nm on its S7 surface.

The space between the dichroic mirror 102 and the total reflection mirror 109 constitutes a light trapping device (Cavity) configured to trap light having a wavelength of 532 nm.

Because the dichroic mirror 102 is situated on a moving stage 103, the optical path length of the light trapping device can be controlled.

The L-shaped space formed by the total reflection mirror 109, the dichroic mirror 105, and the output mirror 111 constitutes an optical resonator (Optical Parametric Oscillation Cavity).

In the optical resonator, each time light having a wavelength of 532 nm passes through an optical parametric crystal 106 on the same optical path, the signal light and the idler light are amplified, and the signal light and the idler light that have exceeded the threshold of the output mirror 111 are output from the output mirror 111 as the pump light (denoted by a dotted-line arrow in FIG. 4) and the Stokes light (denoted by a dashed-line arrow in FIG. 4).

The light trapping device and the optical resonator share the optical parametric crystal 106. Because the total reflection mirror 109 is situated on a moving stage 110, the optical path length of the optical resonator can be controlled. It is possible to make the wavelengths of the pump light and the Stokes light that are generated on the same optical path variable respectively, by changing the angle of the optical parametric crystal 106 using a galvano motor 107 to which a galvano drive signal is input from a galvano power supply 108.

While the time taken by light having a wavelength of 532 nm to go and return in the light trapping device and the time taken by the light to go and return in the optical resonator are made equal to each other by means of the moving stages 103 and 110, the light is excited by being passed through the optical parametric crystal 106 a plurality of times in one pulse period of the light.

By the optical parametric oscillation, the pump light and the Stokes light are output from the output mirror 111 in a state that the pump light and the Stokes light are superposed with each other both spatially and temporally in orthogonal polarization directions.

The pump light and the Stokes light, which are two orthogonally polarized frequencies, become the pump light and the Stokes light that are polarized in the same direction in a 45-degree direction by being passed through a polarizer 112, the optical axis direction of which is inclined by 45 degrees from the orthogonal axes.

Next, an operation for capturing a tomographic image will be described.

The pump light and the Stokes light that are polarized in the same direction in a 45-degree direction are spectrally diffracted by a half mirror 113 respectively.

The pump light and the Stokes light on one side, split in two by the half mirror 113, come incident into the fundus of an eyeball part 20 serving as the test object through galvano mirrors 115 and 116, and are reflected on a refractive index boundary portion of the eyeball part 20 to come incident again into the half mirror 113 as reflected light of the pump light and reflected light of the Stokes light.

The pump light and the Stokes light on the other side, split in two by the half mirror 113, are reflected on a reflection mirror 301, and as reference light for obtaining interference light, are superposed on the half mirror 113 with the reflected light of the pump light and the reflected light of the Stokes light from the test object.

The reference light and the reflected light that are superposed with each other are split into the interference light of the pump light and the interference light of the Stokes light by a long pass dichroic mirror 302 that is configured to reflect light having a wavelength of 1,064 nm or longer. Then, they come incident into photo-detectors 303 and 304 respectively.

Figure 5:
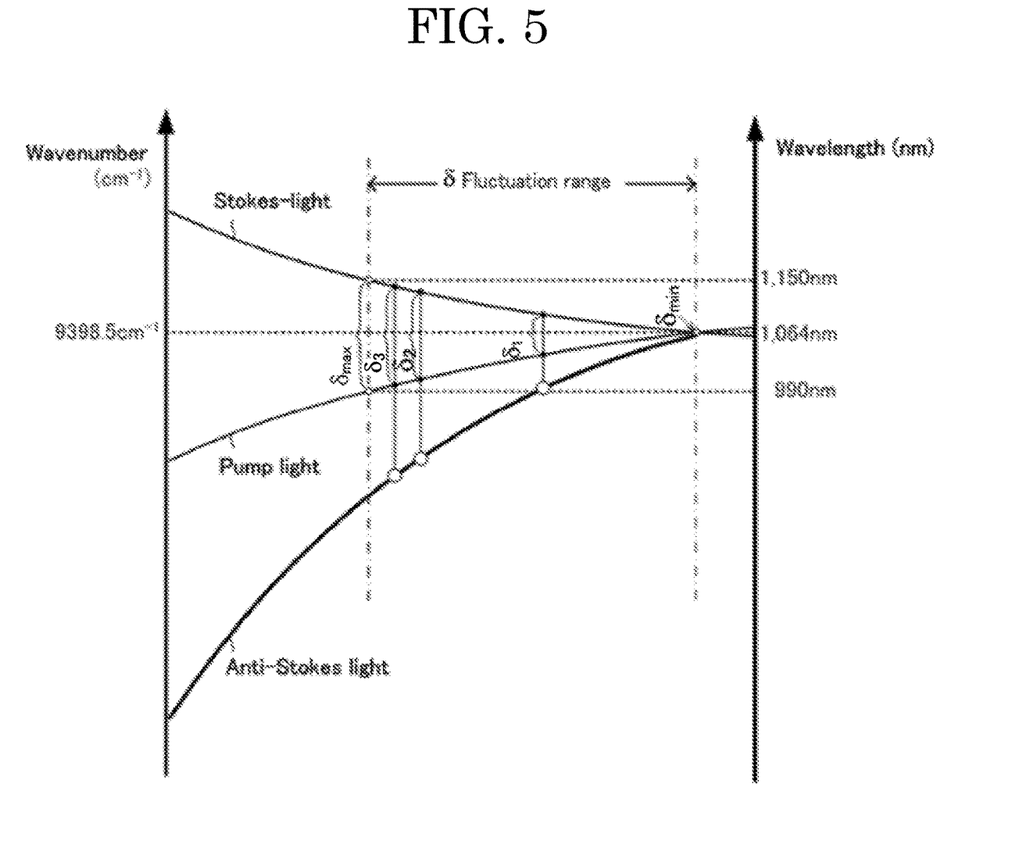
FIG. 5 is a diagram illustrating an example of a relationship among ranges in which wavelengths of pump light and Stokes light are variable, vibration bands of molecules in a test object, and a wavelength of anti-Stokes light.

FIG. 5 is a diagram illustrating an example of a relationship among ranges in which the wavelengths of the pump light and the Stokes light are variable, the vibration bands of molecules in the test object, and the wavelength of the anti-Stokes light.

As illustrated in FIG. 5, the minimum value δ min and the maximum value $\delta_{max}$ of the wavelength difference, which is variable, satisfy the following formula: $0=\delta_{min}<\delta_n<\delta_{max}$, where $\delta_n$ represents the vibration bands of a plurality of molecules in the test target.

Examples of the vibration bands of the molecules in the test object include a 512 cm$^{-1}$ skeletal vibration band $\delta_1$ of glucose, a 1,050 cm$^{-1}$ C—O vibration band $\delta_2$ of retinol, and a 1,159 cm$^{-1}$ C—C vibration band $\delta_3$ of lutein. In this case, it is assumed that the variable wavelength difference is in a range of 0 cm$^{-1}<\delta<1,400$ cm$^{-1}$. The wavelength of the pump light is varied in a range of 990 nm$\leq\lambda_{pump}\leq1,064$ nm, and the wavelength of the Stokes light is varied in a range of 1,150 nm$\geq\lambda_{Stokes}\geq1,064$ nm.

Hence, the photo-detector 303 configured to detect the Stokes light outputs a spectral interference signal in a range of 1,064 nm$\leq\lambda_{Stokes}\leq1,150$ nm, and the photo-detector 304 configured to detect the pump light outputs a spectral interference signal in a range of 1,064 nm$\geq\lambda_{pump}\geq990$ nm.

Both of the spectral interference signals are coupled with each other by the signal processing unit 400 at a wavelength of 1,064 nm at which the wavelength difference becomes 0, to become a spectral interference signal in a range of 990 nm$\leq\lambda\leq1,150$ nm. When an inverse Fourier transform operation is executed on the spectral interference signal, the A-line signal mentioned above for generating the tomographic image, with a depth resolution represented by the following formula: $\Delta z=(2 \ln 2)/\Pi\cdot(\lambda_0^2/\Delta\lambda)=3.16$ micrometers, is obtained. By scanning the measurement of the A-line signal in the X direction, it is possible to obtain the tomographic image. Note that ln stands for natural logarithm, $\lambda_0$ represents the wavelength of the anti-Stokes light, and $\Delta\lambda$ represents the step for sweeping the wavelengths of the pump light and the Stokes light.

Next, an operation for capturing a molecule distribution image will be described with reference to FIG. 4.

The pump light and the Stokes light on the one side, spectrally diffracted by the half mirror 113, are further spectrally diffracted by a half mirror 201.

The pump light and the Stokes light on one side, spectrally diffracted by the half mirror 201, are converged by means of a lens 213 through water 202 serving as a sample for anti-Stokes light emission and a reflection mirror 203 in order to generate reference light for the non-resonant anti-Stokes light. The non-resonant anti-Stokes light induced at the convergent point is reflected on the reflection mirror 203, is condensed through the lens 213, and comes incident again into the half mirror 201 as collimated light.

The pump light and the Stokes light on the other side, split in two by the half mirror 201, come incident into the eyeball part 20 serving as the test object through the galvano mirrors 115 and 116, are converged by the eye lens of the eyeball part 20, and reach the fundus retina. The resonant anti-Stokes light is emitted from a molecule in the test object present in the fundus retina irradiated with the pump light and the Stokes light. The emitted resonant anti-Stokes light is condensed by the eye lens, and as collimated light, is superposed on the half mirror 201 with the non-resonant anti-Stokes light serving as reference light for obtaining interference light.

A long pass dichroic mirror 204 configured to reflect light having a wavelength of 990 nm or longer splits the resonant anti-Stokes light and the non-resonant anti-Stokes light that are superposed with each other from the pump light and the Stokes light that are in the same optical axis direction.

The resonant anti-Stokes light and the non-resonant anti-Stokes light that are split are split by a long pass dichroic mirror 205 configured to reflect light having a wavelength of 950 nm or longer, and anti-Stokes light (984 nm light) in a glucose skeleton vibration mode comes incident into a photo-detector 206 as a glucose resonance signal.

Anti-Stokes light (911 nm light) in a retinol C—O vibration mode and anti-Stokes light (898 nm light) in a lutein C—C vibration mode, which are reflected by the long pass dichroic mirror 205, are split by a long pass dichroic mirror 208 configured to reflect light having a wavelength of 905 nm or longer and come incident into photo-detectors 209 and 211 as a retinol resonance signal and a lutein resonance signal respectively.

As illustrated in FIG. 5, in the range of the variable wavelength difference δ of 0 cm$^{-1}<\delta<1,400$ cm$^{-1}$, the resonant anti-Stokes light (with a wavelength of 984 nm) corresponding to 512 cm$^{-1}$ of glucose skeletal vibration, the resonant anti-Stokes light (with a wavelength of 911 nm) corresponding to 1,050 cm$^{-1}$ of retinol C—O vibration, and the resonant anti-Stokes light (with a wavelength of 898 nm) corresponding to 1,525 cm$^{-1}$ of lutein C—C vibration are emitted in a range of about ±5 nm from the center wavelength of each.

Being superposed on the half mirror 201 with the non-resonant anti-Stokes light serving as the reference light, these resonant anti-Stokes lights are detected by the photo-detectors 206, 209, and 211.

The outputs from the photo-detectors 206, 209, and 211 become spectral interference signals with direct-current components removed by high pass filters 207, 210, and 212.

When an inverse Fourier transform operation is executed on the spectral interference signals, the A-line signals mentioned above for generating the molecule distribution image, with a depth resolution represented by the following formula: $\Delta z=(2 \ln 2)/\Pi\cdot(\lambda_0^2/\Delta\lambda)=(2 \ln 2)/\Pi\cdot(0.9^2/0.01)=35$ micrometer, are obtained. By scanning the measurement of the A-line signals in the X direction, it is possible to obtain the molecule distribution image.

In the existing molecule distribution imaging techniques utilizing the CARS, scanning in the optical axis direction using an optical system with a high numerical aperture is necessary. By executing an inverse Fourier transform operation on the spectral interference signals of the anti-Stokes lights (CARS lights), it is possible to do without the mechanism for performing scanning in the optical axis direction.

By the operations described above, it is possible to simultaneously capture the molecule distribution image and the tomographic image of the test object.

By performing optical scanning not only in the X direction but also in the Y direction, it is possible to simultaneously capture a three-dimensional molecule distribution image and a three-dimensional morphological image of the test object.

REFERENCE SIGNS LIST

10: test object visualizing device
20: eyeball part (test object)

100: light irradiating unit
200: molecule distribution image generating unit
300: tomographic image generating unit
400: signal processing unit
500: image display unit

The invention claimed is:

1. A test object visualizing device, comprising:
a light irradiating unit including an optical parametric crystal configured to change a wavelength of light, the light irradiating unit being configured to make a wavelength of at least any one of pump light and Stokes light variable per test position of a test object through the optical parametric crystal, the pump light and the Stokes light being generated on a same optical axis, the light irradiating unit being configured to irradiate the test object with the pump light and the Stokes light;
a molecule distribution image generating unit configured to detect anti-Stokes light emitted from the test object according to a wavelength difference between the pump light and the Stokes light by a photo-detector, and generate a molecule distribution image based on the anti-Stokes light;
a tomographic image generating unit configured to detect at least any one of reflected light from the test object when the test object is irradiated with the pump light and reflected light from the test object when the test object is irradiated with the Stokes light by a photo-detector, and generate a tomographic image of the test object based on the reflected light detected; and
an image display unit configured to display at least any one of the molecule distribution image and the tomographic image that are generated.

2. The test object visualizing device according to claim 1, wherein the light irradiating unit is configured to irradiate the test object with the pump light and the Stokes light in a manner that the wavelength difference between the pump light and the Stokes light becomes 0 in ranges in which the wavelength of the pump light and the wavelength of the Stokes light are made variable, and
wherein the tomographic image generating unit is configured to generate the tomographic image based on data obtained by merging, at a wavelength at which the wavelength difference becomes 0, data based on the reflected light from the test object when the test object is irradiated with the pump light with data based on the reflected light from the test object when the test object is irradiated with the Stokes light.

3. The test object visualizing device according to claim 1, wherein the molecule distribution image generating unit is configured to execute an inverse Fourier transform operation on a spectral interference signal obtained by spectrally diffracting the anti-Stokes light.

4. The test object visualizing device according to claim 1, wherein the tomographic image generating unit is configured to execute an inverse Fourier transform operation on a spectral interference signal obtained by spectrally diffracting at least any one of the reflected light from the test object when the test object is irradiated with the pump light and the reflected light from the test object when the test object is irradiated with the Stokes light.

5. The test object visualizing device according to claim 1, wherein the light irradiating unit comprises:
a light trapping device that comprises the optical parametric crystal, the light trapping device being configured to trap the light; and
an optical resonator sharing the optical parametric crystal with the light trapping device and configured to amplify light of which wavelength is changed by the optical parametric crystal.

6. The test object visualizing device according to claim 1, wherein the light irradiating unit is configured to make the wavelength of the pump light and the wavelength of the Stokes light variable in a manner that a vibration band of a molecule contained in the test object coincides with the wavelength difference.

7. The test object visualizing device according to claim 6, wherein the molecule contained in the test object is at least any one of glucose, retinol, and lutein.

* * * * *